US008064992B2

(12) United States Patent
Henry et al.

(10) Patent No.: US 8,064,992 B2
(45) Date of Patent: Nov. 22, 2011

(54) ACTIVE IMPLANTABLE MEDICAL DEVICE WITH HOLTER RECORDING FUNCTIONS

(75) Inventors: Christine Henry, Paris (FR); Yann Poezevara, Courcouronnes (FR)

(73) Assignee: ELA Medical S.A.S., Montrouge (FR)

( * ) Notice: Subject to any disclaimer, the term of this patent is extended or adjusted under 35 U.S.C. 154(b) by 209 days.

(21) Appl. No.: 11/004,661

(22) Filed: Dec. 3, 2004

(65) Prior Publication Data
US 2005/0137488 A1 Jun. 23, 2005

(30) Foreign Application Priority Data
Dec. 3, 2003 (FR) ...................................... 03 14158

(51) Int. Cl.
*A61B 5/04* (2006.01)
(52) U.S. Cl. ....................................... 600/513; 600/529
(58) Field of Classification Search ................... 600/484, 600/513, 529; 607/20
See application file for complete search history.

(56) References Cited

U.S. PATENT DOCUMENTS

| | | | | |
|---|---|---|---|---|
| 4,930,506 A * | 6/1990 | Ullrich | ........................... | 600/326 |
| 5,178,151 A * | 1/1993 | Sackner | ........................ | 600/485 |
| 5,187,657 A * | 2/1993 | Forbes | ........................... | 600/513 |
| 5,348,008 A * | 9/1994 | Bornn et al. | ................... | 600/301 |
| 5,353,793 A * | 10/1994 | Bornn | ............................. | 600/386 |
| 5,722,999 A * | 3/1998 | Snell | ................................. | 607/32 |
| 5,765,563 A * | 6/1998 | Vander Schaaf | .............. | 600/538 |
| 5,902,250 A * | 5/1999 | Verrier et al. | .................. | 600/515 |
| 6,200,265 B1 * | 3/2001 | Walsh et al. | ................... | 600/300 |
| 6,351,670 B1 * | 2/2002 | Kroll | ................................. | 607/5 |
| 6,409,675 B1 * | 6/2002 | Turcott | ........................... | 600/508 |
| 6,589,188 B1 * | 7/2003 | Street et al. | .................... | 600/538 |
| 6,662,032 B1 * | 12/2003 | Gavish et al. | ................. | 600/323 |
| 6,858,006 B2 * | 2/2005 | MacCarter et al. | ............ | 600/300 |
| 7,025,729 B2 * | 4/2006 | de Chazal et al. | ............. | 600/508 |

(Continued)

FOREIGN PATENT DOCUMENTS
EP 0 653 226 A1 11/1994

*Primary Examiner* — Niketa Patel
*Assistant Examiner* — Hiba El-Kaissi
(74) *Attorney, Agent, or Firm* — Orrick Herrington & Sutcliffe, LLP

(57) ABSTRACT

This device collects and analyzes general data on the state of the patient, and collects continuously a monitored signal representative of a physiological function. It includes a memory with a first zone for the durable memorizing of these data, and analyzes in real time the monitored signal to detect there the occurrence of a particular event. The memory includes a second zone for the continuous memorizing of the monitored signal over a first period of time, the memorizing being started on detection of a particular event. The device can also collect context information representative of circumstances possibly related to the occurrence of the particular event. The memory then includes a third zone, for the conditional memorizing of this information on detection of an event, for a second period of time shorter than the first period. The monitored signal can, for example, be a ventilatory signal, in which case the event is a hypopnea and/or a apnea, the context information include a ventricular and/or atrial electrogram, events markers of the heartbeat rate and/or a signal of the peak endocardial acceleration. The monitored signal can be also an electrogram signal, a signal of the peak endocardial acceleration, a series of events markers of the heartbeat rate and/or an intracardiac signal of bio-impedance. The event is then a preset disorder of the heartbeat rate and/or a disorder of atrio-ventricular conduction, the context information include the events markers of the heartbeat rate, a signal of the peak endocardial acceleration and/or a ventilatory signal.

24 Claims, 1 Drawing Sheet

U.S. PATENT DOCUMENTS

| | | |
|---|---|---|
| 2002/0082867 A1* | 6/2002 | MacCarter et al. ............... 705/2 |
| 2002/0173829 A1 | 11/2002 | Graindorge ..................... 607/59 |
| 2002/0193697 A1 | 12/2002 | Cho et al. ....................... 600/529 |
| 2002/0198473 A1* | 12/2002 | Kumar et al. .................. 600/595 |
| 2003/0055348 A1* | 3/2003 | Chazal et al. .................. 600/509 |
| 2004/0077934 A1* | 4/2004 | Massad ......................... 600/300 |
| 2004/0088027 A1* | 5/2004 | Burnes et al. ................... 607/60 |
| 2005/0131288 A1* | 6/2005 | Turner et al. .................. 600/391 |

* cited by examiner

ACTIVE IMPLANTABLE MEDICAL DEVICE WITH HOLTER RECORDING FUNCTIONS

FIELD OF THE INVENTION

The present invention relates to "active implantable medical devices" as defined by the Jun. 20, 1990 directive 90/385/CEE of the Council of the European Communities. The invention relates to active implants such as cardiac pacemakers, cardiovertors and/or defibrillators or multisite devices, i.e., apparatuses able to apply an antibradycardic and/or antitachycardic therapy to one or more chambers of the heart, but it also can be implemented in implants whose only object is the follow-up and recording of physiological parameters, like the one described in WO-A-98/02209 (Medtronic Inc).

BACKGROUND OF THE INVENTION

The invention more precisely relates to those devices that are equipped with Holter functions, i.e., with functions for recording over a long time period, from several days to several months, data collected by the device, typically data relating to the cardiac or ventilatory activity of the patient. Information thus recorded can be transmitted later on, by telemetry, with an ancillary device or "programmer" for display and analysis.

The physiological signals collected by these implants can be of very different natures:
- signals representative of the cardiac activity and the heartbeat rate measured by means of atrial and/or ventricular implanted electrodes—these signals are usually called "electrograms," as opposed to "electrocardiograms" collected by external electrodes;
- signals representative of respiratory activity, for example, the minute ventilation signal obtained by measurement of the transthoracic impedance taken between the metal case of the device and a distant electrode;
- signals representative of blood flow or myocardium contractility, obtained from an intracardiac measurement of impedance (e.g., transvalvular, between two cavities located on the same side of the heart, or trans-septum impedance, inter-ventricular or oblique impedance, taken between two cavities located on two different sides);
- signals of measurement of the oxygen saturation in blood, or of measurement of the blood pH, etc.

One will include in this concept of "signals" not only the signals themselves collected by electrodes, but also the event markers of the heartbeat rate, event counters, or signals not collected but representative of a state or an action of the implant, for example, the application of a therapy, or a commutation of operating mode, etc.

EP-A-0 653 226 and its counterpart, U.S. Pat. No. 5,513,645, commonly assigned herewith to ELA Medical, describes such an implantable device—a cardiovertor, equipped with Holter recording functions able to operate a memorization of data on several levels of detail: in the case of an event (e.g., occurrence of a disorder of the rate, application of a therapy . . . ), the device records throughout a short period more detailed information (typically, an electrogram sample of the period having preceded and/or followed the particular event), while the remainder of time it records simply a chain of markers.

In this known device, as in the other implants integrating the Holter functions of recording, almost all the memory—whose size is necessarily limited because of the constraints of miniaturization and of power consumption—is reserved for the memorizing of information concerning the many algorithms and available functions such as statistics, histograms, electrogram episodes, markers triggered on particular events, etc. It is the reason for which the above mentioned EP-A-0 653 226 and U.S. Pat. No. 5,551,645 propose memorizing the electrogram only over a very short duration, limited to the moments preceding and following the triggering of a therapy, typically the two seconds preceding and following the cardioversion or defibrillation shock.

In certain circumstances, however, it can be useful to collect and memorize a significant volume of information, dedicated to a particular function, for a long given period, for example, over 24 hours.

One of the goals of the present invention is to propose an implant equipped with Holter recording functions that can be dedicated at will to the continuous recording in real time of a particular function.

Thus, for example, for the study of disorders related to sleep apnea, it would be interesting to be able to monitor continuously and over 24 hours, or at the very least for part of the night, the entirety of the minute-ventilation signal. Also, for disorders of the heartbeat rate or evaluation of atrio-ventricular conduction, it would be interesting to be able to safeguard continuously the totality of the electrogram over 24 hours, to be able later on to analyze it in same manner as an electrocardiogram recording produced by an external device connected to surface electrodes.

The basic idea of the invention consists in envisaging an implantable device whose Holter memory can be used either in a standard way (i.e., by memorizing the usual data such as statistics, histograms, markers, etc), or in a way dedicated to the follow-up of a particular function.

In the dedicated Holter configuration, the apparatus devotes the major part of its memory to the continuous recording of the chosen signal, preserving only some bytes for general information on the other functions of the apparatus. The implanted device of the invention not only monitors the recorded signal, preferably continuously, but, moreover, analyzes this collected signal in real time.

In the example where the recorded signal is a ventilatory signal, this analysis makes it possible to identify certain events such as apnea, hypopnea, or respiratory pauses, or the particular respiratory profiles, such as profiles of the Cheyne-Stokes type. One will be able to refer in this respect to EP-A-0 970 713 and its counterpart, U.S. Pat. No. 6,574,507, EP-A-1 336 422 and its counterpart U.S. Published Application No. 2004/0063375, and EP-A-1 295 623 and its counterpart U.S. patent application Ser. No. 10/255,144, all in the name of ELA Médical.

In the example where the monitored signal is a cardiac signal, the analysis makes it possible to identify events such as an arrhythmia or a disorder of conduction. The detection of these events then triggers memorization of one or more pieces of "context information," i.e., of parallel information, distinct from the monitored signal, which will make it possible to study later the context of occurrence of the events, in particular for the purpose of diagnosis. For example, if the monitored signal is the ventilatory signal, context information could be an electrogram episode, a signal of the peak endocardial acceleration, a signal delivered by a sensor of activity such as an accelerometer integrated into the case of the device, or any other information making it possible to document the event (apnea, hypopnea . . . ) detected on the monitored signal.

OBJECTS AND SUMMARY OF THE INVENTION

The present invention proposes an active implantable medical device with Holter recording functions of the type described by above-mentioned EP-A-0 653 226, i.e., including means for collecting data relating to the state of the patient carrying the device and/or operation of this device and to analyze the collected data to produce in response representative general information, means for continuous collection of at least one monitored signal, representative of a physiological function of the patient, a data memory means, where are memorized in a durable way the aforementioned general information, and means for analyzing in real time the monitored signal, to detect the occurrence of at least a particular event.

In a characteristic way, the device includes means for processing the collected data, operative in response to the means for analyzing, to organize the memory, on detection of the occurrence of at least one particular event, in a first zone, for memorizing the aforesaid general information and a second zone, for continuously memorizing the aforesaid monitored signal, and means able, on detection of the occurrence of the aforesaid particular event by the analyzing means, to start the aforementioned continuous memorization of the monitored signal in the second storage area for a first period of time.

In a preferred embodiment, the device also includes means for dynamically allocating the second zone, able to commutate the device between a standard configuration, where the second zone is allocated to memorizing a plurality of general information in complement of the first zone, and a dedicated configuration, where the second zone is allocated to a continuous memorization of the monitored signal.

Triggering means can, on reception of a command, commutate the device to a dedicated configuration and begin continuously memorizing the monitored signal in the second zone. This command can be a signal indicating a beginning of phase of sleep of the patient, a signal indicating the crossing of a preset threshold by the heart rate, a command of external origin transmitted to the device by the patient or by a physician, and/or a pre-programmed internal command generated by the device.

In a general way, the second zone can possibly include the first zone.

In yet another preferred embodiment, the device also includes means for collecting context information, representative of circumstances possibly related to the occurrence of the particular event. The device further includes means for collecting the context information, and means for processing the memory operates in response to the analyzing means to organize the memory, in addition to the first zone and the second zone, in a third zone, for conditional memorization of the aforesaid context information. The device also includes means able, on detection on the occurrence of the aforesaid particular event by the analyzing means, to start the aforementioned memorizing of the context information in the third storage zone, for a second period of time shorter than the aforementioned first period of memorizing the monitored signal.

The monitored signal can be in particular a ventilatory signal, in which case the particular event whose occurrence is detected by the means for analyzing is a hypopnea and/or an apnea and/or a repetitive predetermined template of the respiratory signal, and the context information includes a ventricular and/or atrial electrogram signal, event markers of the heartbeat rate, and/or a signal of the peak endocardial acceleration.

The monitored signal can also be a ventricular and/or atrial electrogram signal, a signal of the peak endocardial acceleration, a series of event markers of the heartbeat rate, and/or an intracardiac signal of bio-impedance.

In one useful embodiment, the particular event for which occurrence is detected by the analyzing means is a preset disorder of the heartbeat rate and/or a disorder of atrio-ventricular conduction, and context information includes event markers of the heartbeat rate, a signal of the peak endocardial acceleration and/or a ventilatory signal.

The device also includes means for tele-transmitting to an external programmer the contents of the second zone, as well as contents of the third zone if context information were memorized, for subsequent display and analysis by the programmer. It is envisaged also to have suitable means to erase the second and the third zones of memory after tele-transmission of their contents, in order to authorize later memorizing newly acquired data, and means for commutating the device to a standard configuration after a tele-transmission.

The first and/or the second period of time can be predetermined periods of time. The first period of time, for example, 24 hours, can be one single continuous period, or a period split into a plurality of daily sub-periods; the second period of time is then, for example, 10 seconds in relation to the moment of the occurrence of the aforesaid particular event. The first and/or the second period of time can also be periods of time lasting until saturation of the data in the memory means, or undetermined periods, the new data being recorded in the data memory until filled and with new data then replacing the older data.

BRIEF DESCRIPTION OF THE DRAWINGS

Further features, characteristics and advantages of the present invention will become apparent to a person of ordinary skill in the art from the following detailed description of a preferred embodiment of a device of the present invention, made with reference to the annexed figures, on which the same reference numbers represent identical or functionally similar elements, and in which.

DETAILED DESCRIPTION OF THE INVENTION

Figure 1:
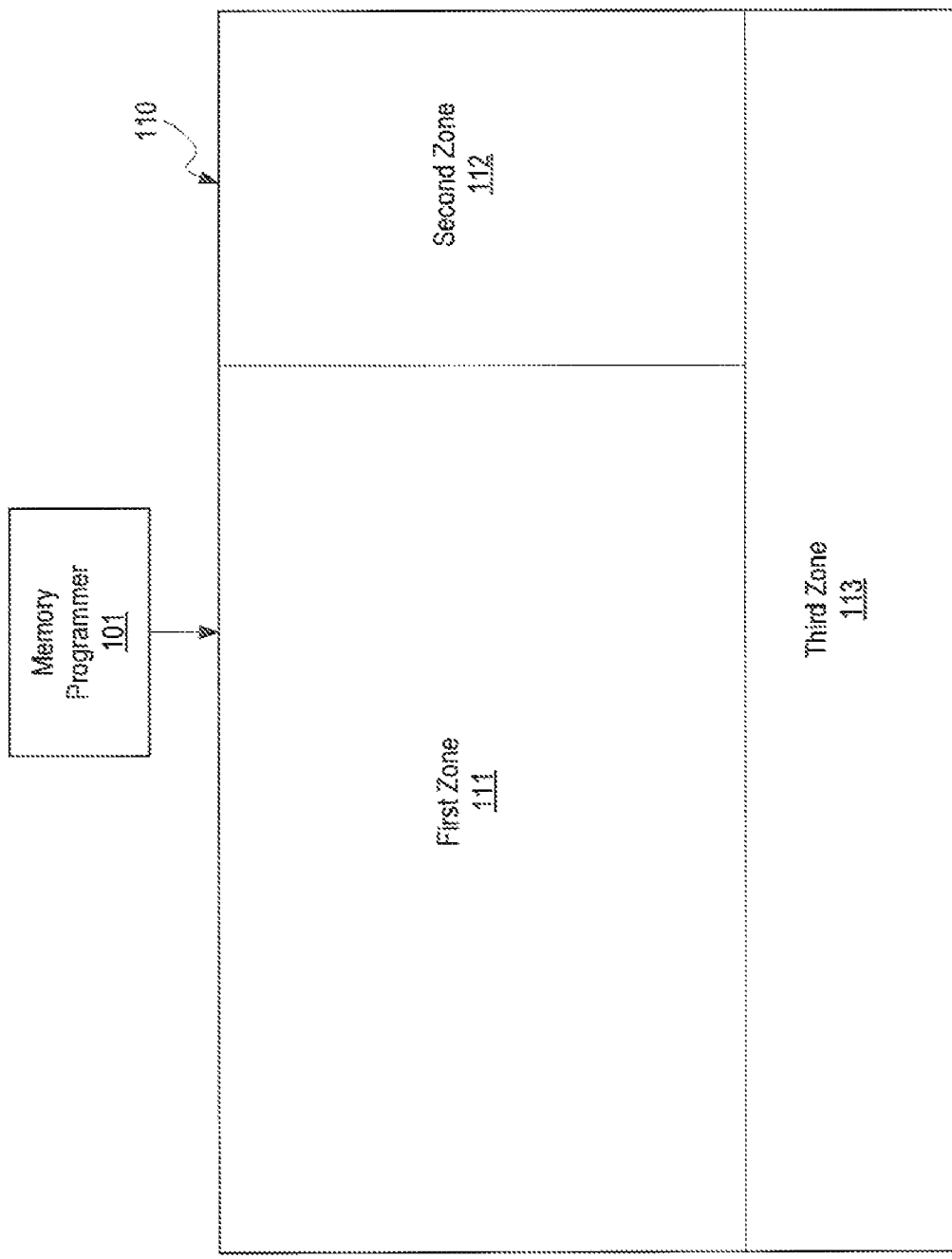
FIG. 1 illustrates a schematic diagram for a memory of implantable medical device, according to one embodiment.

One now will describe in more detail the invention, which can be implemented by suitable programming of the control software of a device of a type in itself known, for example, a cardiac pacemaker or a defibrillator, including any suitable means for acquisition of a signal provided by implanted endocavitary probes and/or one or more sensors.

The invention can in particular be applied to the devices marketed by ELA Médical, Montrouge, France. This include devices with microprocessor comprising circuits to receive, to format, and to process electric signals collected by implanted electrodes. It is possible to download by telemetry software which will be stored and executed to implement the functions of the invention, which will be described below.

The various signals provided by the endocavitary implanted probes and/or sensors can be in particular:
  ventricular and/or atrial electrogram signals;
  event markers of the heartbeat rate, produced by an analysis algorithm internal to the device;
  a signal of the peak endocardial acceleration, by use of an accelerometer sensor as described, for example, in EP-A-0 515 319 (assigned to Sorin Biomedica Cardio Spa);
  a signal representative of the respiratory activity of the patient, typically a minute-ventilation signal obtained by measurement of the transthoracic impedance between the case of the pacemaker and an endocavitary electrode;

a signal representative of the blood flow, typically obtained by a measurement of bio-transvalvular impedance (between atrium and ventricle located on the same side of the heart), trans-septum oblique (between a ventricle and the atrium located on the opposite side) or interventricular trans-septum (between the two ventricles), giving a value correlated to the cardiac flow and the myocardium contractility; or a signal delivered by an activity sensor of the patient such as an accelerometer integrated into the case of the device.

In a characteristic way, the device includes means to program a memorization of Holter data:

in a "standard" mode, i.e., for a simple memorization of statistics, histograms, markers, counters of events, short episodes of electrograms on appearance of a particular event, etc., over a very long duration, for example, from several days to several months, and relating to all the functions available in the implanted device (prevention of atrial fibrillations, fall-back, atrio-ventricular conduction, etc. ); or in a mode known as "dedicated", in accordance with the present invention. In the dedicated mode, the Holter memory will be used to memorize continuously a particular signal for a predetermined length of time; this particular signal not only will be memorized for the period considered, but will also be analyzed continuously in real time by the device to detect the possible occurrence of a predetermined event, and for this reason will be indicated "monitored signal."

The monitored signal can, for example, be:

the minute-ventilation signal, if one wants to dedicate the apparatus to the analysis of a respiratory disorder (e.g., sleep apnea, hypopnea); or the electrogram, if one wants to temporarily dedicate the apparatus to the analysis of a disorder of the heartbeat rate or of the atrio-ventricular conduction.

The monitored signal will be completely stored in the Holter memory over a 24 hour duration, for example, a duration that can be a 24 hour continuous period, or a split period, for example, 6 sub-periods, with each period lasting 6 hours, repeated 4 times during 4 consecutive nights.

The passage from the standard mode to the dedicated mode, and thus the triggering of the storage of the monitored signal, are carried out either at will, by a command sent by telemetry to the device by the patient or by a physician, or in an automatic way on detection of certain conditions. This automatic passage to the dedicated mode can, for example, be started by:

a signal indicating a beginning of a phase of sleep of the patient, resulting from an internal clock setting an indicator at a fixed hour or time, or obtained by analysis of the physiological minute-ventilation signal to discriminate between awakening and sleep phases, as is taught by EP-A-0 719 568 and its counterpart, U.S. Pat. No. 5,622,428 (assigned herewith ELA Médical); or a signal indicating the crossing of a threshold, for example, when the heart rate exceeds a predetermined higher limit.

As indicated above, the monitored signal is analyzed in real time by the device in order to detect the possible occurrence of events such as, but not limited to:

apnea or hypopnea, for a ventilatory signal;

modification of morphology on the electrogram, for an endocavitary cardiac signal;

arrhythmia, for markers or based upon the electrogram;

change of average amplitude, for an intracardiac signal of endocardial acceleration or bio-impedance;

detection of a particular repetitive variation profile of the respiratory signal, for example, a profile of the Cheyne-Stokes type, as described, for example, in EP-A-1 295 623 (ELA Médical) mentioned above; and amplitude drops of the peak endocardial acceleration, etc.

On detection of an event, the device starts the parallel recording, over a short duration, of additional context information. The detection of these events can also be used to start the automatic passage in dedicated mode.

Additional context information is, for example:

an episode of electrogram and/or endocavitary acceleration and/or markers of events, on detection of an apnea based from the ventilatory signal; or recording of markers and/or the values of the peak of endocardial acceleration and/or of a ventilatory signal episode, on detection of an arrhythmia based from the electrogram.

The duration of recording of context information, for example, is 10 seconds duration in relation to the moment on the occurrence of the detected event.

FIG. 1 illustrates a schematic diagram for a memory of implantable medical device, according to one embodiment. Memory programmer 101 configures memory 110 of an implantable medical device in response to a triggering signal. Upon receiving the triggering signal, memory programmer 101 commutates the configuration of the memory 110 between a standard mode and a dedicated mode.

For example, in a standard mode, memory programmer 101 may configure memory 110 to store general information such as statistics, histograms, markers, counters of events, short episodes of electrograms on appearance of a particular event, etc. In a standard mode, general information can be stored over a long duration, for example, from several days to several months. The interval of the data storage in a standard mode may be sparser than a dedicated mode to accommodate data over a longer period of time.

In a dedicated mode; memory programmer 101 may configure memory 110 to store only monitored signal in a second zone 112 without allocating a first zone 111. Either in a standard mode or a dedicated mode, memory programmer 101 may configure memory 110 to have both the first zone 111 and the second zone 111 and the size thereof is dynamically allocated for optimal data storage in memory 110. When a new space is needed for monitored signal, older general information may be deleted to make a room for second zone 112 to store new monitored signal.

According to one embodiment, memory programmer 101 may configure memory 110 to include a third zone 113 to store additional context information on detection of an event. When a need arises for a certain data type, a corresponding memory zone may be newly created or expanded dynamically at the sacrifice of another data type, which is older or of less importance.

The monitored signal recorded in the Holter memory, as well as the context information recorded on detection of a particular event, are transmitted later on to an external programmer, by telemetry, in order to be subsequently visualized and processed.

The physician will be able to reach simultaneously, by use of the programmer, the following information:

a curve over 24 hours (i.e., the period of memorizing of the monitored signal) representing a summary of the memorized signal, on which curve can be located, manually or automatically, detected events related to the signal, for example, apnea and hypopnea if the memorized signal is the ventilatory signal; or a "zoom" of the signal when an event is located, or anywhere on the curve of the monitored signal, as, if necessary, the context information which could be memorized on detection of a particular event.

The delayed processing makes it possible to apply to the monitored signal, which was continuously memorized, complex additional processing, making it possible to extract information that it would not have been possible to obtain in real time by means of the implant: e.g., Fourier analysis, sinusal variability, stimulation of algorithms of detection of events, etc.

Advantageously, after the information stored in the Holter memory in dedicated mode has been tele-transmitted to the programmer, the transmission controls the erasing of the memory (because it is no longer necessary to store the information in the implant once it was transmitted and stored outside), and there is an automatic switching of the device in standard operating mode.

Lastly, described above was the process for recording of the data operated over a predetermined duration. But other implementations are possible in alternative, for example, a recording of the monitored signal and/or the context information over a duration until saturation of the data memory, or over an unspecified duration, the new data being recorded in the data memory until it is filled with the new data replacing the older data then, following the well-known "first in, first out (fifo)" technique.

The creation of suitable software instructions for controlling an implant to perform the aforementioned functions of the present invention are believed to be within the abilities of a person of ordinary skill in the art.

One skilled in the art will appreciate that the present invention can be practiced by other than the described embodiments, which are presented for purposes of illustration and not of limitation.

We claim:

1. An active implantable medical device with Holter recording functions, comprising:
    means for collecting data relating to a state of a patient carrying the device and/or operation of the device;
    means for analyzing the collected data relating to the state of the patient to produce general representative information;
    means for continuous collection of a monitored signal representative of a physiological function of the patient;
    a data memory means internal to the device;
    means for analyzing the monitored signal in real time to detect an occurrence of a particular physiological event of the patient; and
    means for programming the data memory means,
    wherein the means for programming is configured to commutate the data memory means between a standard mode and a dedicated mode on detection of the occurrence of the particular physiological event, and
    wherein, in the standard mode, the means for programming also is configured to record the general representative information in a first zone of the data memory means, and in the dedicated mode, the means for programming is configured to dynamically allocate a second zone in the data memory means and record the monitored signal representative of said physiological function in the second zone for a first period of time while continuing to store the general representative information in the first zone.

2. The active implantable medical device of claim 1, further comprising means for receiving a signal from an external origin by telemetry, wherein the triggering signal is a command received by the means for receiving from the patient or a physician.

3. The active implantable medical device of claim 1, wherein the particular physiological event is determined by the group of signals consisting of a signal indicating a beginning of phase of sleep of the patient; a signal indicating a crossing of the patient's heart rate over a preset threshold; and a pre-programmed internal command generated by the means for analyzing in response to the monitor signal.

4. The active implantable medical device of claim 1, wherein the second zone reconfigures at least a portion of the first zone to record the monitored signal in the dedicated mode.

5. The active implantable medical device of claim 1 further comprising:
    means for collecting a context information associated with the particular physiological event, wherein the means for programming allocates a third zone in the data memory means in addition to the first zone and the second zone, for conditional memorizing of the context information, and
    wherein the context information is recorded in the third zone for a second period of time shorter than the first period of time.

6. The active implantable medical device of claim 1, wherein the monitored signal representative of a physiological function of the patient is a ventilatory signal.

7. The active implantable medical device of claim 5, wherein the occurrence of the particular physiological event detected by the means for analyzing is a hypopnea.

8. The active implantable medical device of claim 5, wherein the occurrence of the particular physiological event detected by the means for analyzing is an apnea.

9. The active implantable medical device of claim 5, wherein the occurrence of the particular physiological event detected by the analyzing means is a repetitive predetermined template of a respiratory signal.

10. The active implantable medical device of claim 1, wherein said monitored signal representative of a physiological function of the patient comprises at least one of:
    a ventricular electrogram;
    an atrial electrogram;
    a peak endocardial acceleration;
    at least one event marker of the heartbeat rate; and
    an intracardiac bio-impedance.

11. The active implantable medical device of claim 10, wherein said occurrence of the particular physiological event detected by the analyzing means is a preset heartbeat rate.

12. The active implantable medical device of claim 11, wherein said occurrence of the particular physiological event detected by the analyzing means is a disorder of an atrio-ventricular conduction.

13. The active implantable medical device of claim 1, further comprising means for tele-transmitting to an external programmer contents of the second zone, for subsequent display and analysis by the external programmer 14. The active implantable medical device of claim 13, further comprising:
    means for collecting a context information associated with the particular physiological event;
    means for processing the data memory means, operative in response to the means for analyzing, to organize the data memory means to comprise, in addition to the first zone and the second zone, a third zone, for conditional memorizing of the context information, wherein on detection of the occurrence of the particular physiological event by the means for analyzing, the context information is recorded in the third zone for a second period of time shorter than the first period of time; and wherein the content of the second zone and the third zone are erased after tele-transmission to the external programmer, for authorizing therein memorizing of new data.

15. The active implantable medical device of claim 13, further comprising:

means for collecting a context information associated with a particular physiological event;

means for processing the data memory means, operative in response to the means for analyzing, to organize the data memory means to comprise, in addition to the first zone and the second zone, a third zone, for conditional memorizing of the context information, wherein on detection of the occurrence of the particular physiological event by the means for analyzing, the context information is recorded in the third zone for a second period of time shorter than the first period of time, and wherein the means for tele-transmitting transmits to the external programmer contents of the second zone and the third zone for subsequent display and analysis by the external programmer.

16. The active implantable medical device of claim 15, wherein the contents of the second and third zones are erased in response to the tele-transmission of the contents for authorizing therein memorizing of new data.

17. The active implantable medical device of claim 5, wherein the first period and the second period are predetermined periods of time.

18. The active implantable medical device of claim 17, wherein the first period of time is a single continuous period.

19. The active implantable medical device of claim 18, wherein the first period of time is a period split into a plurality of daily sub-periods.

20. The active implantable medical device of claim 18, wherein the first period of time is a 24 hour period.

21. The active implantable medical device of claim 18 wherein the second period of time is a period in relation to a moment of the occurrence of the particular physiological event.

22. The active implantable medical device of claim 17, wherein the second period of time is a 10 second period.

23. The active implantable medical device of claim 5, wherein the first period and the second period of time are periods of time that last until saturation of the data in memory.

24. The active implantable medical device of claim 5, wherein the first period and the second period of time are unspecified periods of time, whereby new data is recorded in the data memory means until filled and the subsequent new data then replaces the older recorded data.

* * * * *